United States Patent [19]

Davis

[11] Patent Number: 5,064,927
[45] Date of Patent: Nov. 12, 1991

[54] AROMATIC DIAMINES

[75] Inventor: Robert L. Davis, Baton Rouge, La.

[73] Assignee: Ethyl Corporation, Richmond, Va.

[21] Appl. No.: 592,191

[22] Filed: Oct. 3, 1990

Related U.S. Application Data

[62] Division of Ser. No. 254,856, Oct. 7, 1988, Pat. No. 4,973,760.

[51] Int. Cl.$^5$ ............................................. C08G 18/32
[52] U.S. Cl. .......................................... 528/64; 528/68
[58] Field of Search ..................................... 528/64, 68

[56] References Cited

U.S. PATENT DOCUMENTS

| | | | |
|---|---|---|---|
| 4,526,905 | 7/1985 | Lucast et al. | 528/64 |
| 4,549,007 | 10/1985 | Lin et al. | 528/64 |
| 4,611,045 | 9/1986 | Ihrman | 528/76 |
| 4,816,543 | 3/1989 | Burgoyne, Jr. et al. | 528/80 |
| 4,973,760 | 11/1990 | Davis | 528/64 |
| 4,975,516 | 12/1990 | Heile et al. | 528/64 |

Primary Examiner—John Kight, III
Assistant Examiner—Rabon Sergent
Attorney, Agent, or Firm—Richard J. Hammond

[57] ABSTRACT

Novel aromatic diamines which are useful as chain extenders for urethane and urea polymers are compounds corresponding to the formula:

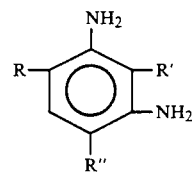

wherein two of the R, R', and R" substituents are alkyl groups containing 1-6 carbons and the other substituent is a hydrocarbylthio group containing 1-6 carbons.

8 Claims, No Drawings

AROMATIC DIAMINES

This application is a division of application Ser. No. 254,845, filed Oct. 7, 1988, now U.S. Pat. 4,973,760.

FIELD OF THE INVENTION

This invention relates to aromatic diamines and more particularly to substituted meta-phenylenediamines which can be used as chain extenders for urethane and urea polymers.

BACKGROUND

As disclosed in U.S. Pat. No. 4,146,688 (Schwindt et al.), it is known that phenylenediamines which bear a single ar-hydrocarbylthio substituent and optionally also a single ar-alkyl substituent can be used as chain extenders for poly-urethane resins. However, the use of these known chain extenders can create toxicity and/or discoloration problems.

U.S. Pat. No. 4,595,742 (Nalepa et al.) discloses phenyl-enediamine chain extenders which bear at least two ar-alkylthio substituents and preferably also an ar-alkyl substituent. These chain extenders lack the disadvantages of the chain extenders of Schwindt et al. and are ordinarily quite suitable for the preparation of urethane and urea polymers having desirable properties. However, in some applications, e.g., in the preparation of room temperature coatings and in the preparation of polymers by RIM processes, the gel times provided by the chain extenders are sometimes slower than is desired.

U.S. Pat. Nos. 4,594,453 (Ranken et al.), 4,670,598 (Davis-I), and 4,751,330 (Davis-II) teach that phenylenediamines bearing at least one ar-hydrocarbylthio substituent can be prepared by reacting a phenylenediamine, optionally bearing an ar-alkyl substituent, with a hydrocarbyldisulfide in the presence of a Lewis acid catalyst.

SUMMARY OF THE INVENTION

An object of this invention is to provide novel meta-phenylendediamines.

Another object is to provide such diamines which are useful as chain extenders for urethane and urea polymers.

A further object is to provide such chain extenders which can be used in RIM processes and in the preparation of room temperature coatings.

These and other objects are attained by the provision of meta-phenylenediamines corresponding to the formula:

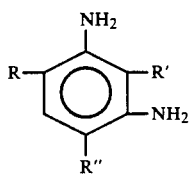

wherein two of the R, R', and R" substituents are alkyl groups containing 1-6 carbons and the other substituent is a hydrocarbylthio group containing 1-6 carbons.

DETAILED DESCRIPTION

The meta-phenylenediamines of the invention may be any compounds corresponding to the above formula, i.e., compounds wherein each of the alkyl groups may be any alkyl group containing 1-6 carbons, such as a methyl, ethyl, propyl, n-butyl, sec-butyl, t-butyl, pentyl, or hexyl group, and the hydrocarbylthio group is one in which the hydrocarbyl moiety may be any saturated or unsaturated aliphatic, alicyclic, or aromatic hydrocarbyl moiety containing 1-6 carbons, such as a methyl, ethyl, propyl, n-butyl, sec-butyl, t-butyl, pentyl, hexyl, allyl, methallyl, cyclopentyl, cyclohexyl, or phenyl group. However, the preferred meta-phenylenediamines are those wherein two of the R, R', and R" substituents are alkyl groups containing 1-3 carbons and the other substituent is an alkylthio group containing 1-3 carbons.

Exemplary of the preferred meta-phenylenediamines are the 2-alkylthio-4,6-dialkyl-1,,3-diaminobenzenes such as 2-methyl-thio-4,6-dimethyl-1,3-diaminobenzenes, 2-ethylthio-4,6- dimethyl-1,3-diaminobenzene, and 2-methylthio-4,6-diisopropyl-1,3-diaminobenzene; the 4-alkylthio-2,6-dialkyl-1,3-diaminobenzenes such as 4-methylthio-2,6-dimethyl-1,3-diaminobenzene, 4-ethylthio-2,6-dimethyl-1,3-diaminobenzene, and 4-methylthio-2,6-diisopropyl-1,3- diaminobenzene; and mixtures thereof.

The compounds of the invention may be prepared by known techniques, such as by using the processes of Ranken et al., Davis-I, or Davis-II (the teachings of all of which are incorporated herein in toto by reference) to substitute a hydrocarbylthio group onto the ring of a 2,6- or 4,6-dialkyl-1,3-diaminobenzene which, when not commercially available, may be prepared by the alkylation of meta-phenylenediamine or by the nitration and reduction of the appropriate dialkylbenzene, as in U.S. Pat. No. 4,526,905 (Lucast et al.), the teachings of which are also incorporated herein in toto by reference. However, they may also be prepared by a modification of the Ranken et al./Davis-I/-Davis-II hydrocarbylthiation processes utilizing an iodine catalyst or a nitrogen sparge, as taught in copending applications Ser. No. 254,857, filed Oct. 7, 1988 (abandoned) and copending application Ser. No. 552,892, filed July 16, 1990, now U.S. Pat. No. 5,015,770. Ser. No. 254,858, filed Oct. 7, 1988 (abandoned), respectively. Use of the nitrogen sparge technique is apt to be preferred when a hydrocarbyldisulfide having more than one carbon in the hydrocarbyl moiety is used to substitute a hydrocarbylthio group onto the ring of the dialkyl-1,3-diaminobenzene.

The meta-phenylenediamines of the invention are particularly useful as chain extenders for urethane, urea, and urethane-urea polymers which, like those of the prior art, are prepared by reacting the chain extender with (1) an organic polyisocyanate and an active hydrogen-containing organic compound or (2) a prepolymer thereof having a free -NCO content of at least 0.1% by weight. The organic polyisocyanates and active hydrogen-containing organic compounds, or prepolymers thereof, which are reacted with the chain extenders may be any such materials which are conventionally employed in the preparation of urethane, urea, anc urethane-urea polymers, such as those taught in Nalepa et al., the teachings of which are incorporated herein in toto by reference. However, since a particular advantage of the novel chain extenders is their providing gel times which are slower than those obtained- with very reactive chain extenders, such as dialkyltoluenediamines, and faster than those obtained with relatively slow chain extenders, such as di(alkylthio)toluene-diamines, they are especially of interest for use in the preparation of room temperature coatings and in the preparation of polymers by RIM processes —applications in which the materials reacted with chain extenders are generally dipheny-methanediisocyanate (MDI) or toluendiisocyanate (TDI) prepolymers.

The following examples are given to illustrate the invention and are not intended as a limitation thereof.

EXAMPLE I

Part A

A suitable reaction vessel was charged with 7.9L of a 5.5/1 by volume mixture of concentrated sulfuric acid and 90% nitric acid. After the acid mixture had been cooled to −10° C., 1970g of 1,3-diisopropylbenzene was added with stirring at a rate such as to maintain a reaction temperature between 31 10° C. and 0° C., stirring was continued for an additional two hours, and the reaction mixture was then allowed to warm to ambient temperature. The excess acid was then diluted to about 25-30% by the addition of ice, after which the solid product was filtered by suction and washed once with water, once with 5% aqueous sodium carbonate, and once again with water.

PART B

The moist solid product of Part A was charged to a suitable reaction vessel, followed by 17L of toluene and 40g of 5% Pd/C catalyst. The solid was then hydrogenated at 95° C. and 5.2 MPa of hydrogen to convert the nitro groups in the starting material to amino groups. After hydrogenation was complete, the catalyst was removed by filtration and the toluene stripped in a rotary evaporator. The residue was vacuum-distilled from 1% solid NaOH. The reaction resulted in the formation of 1436g (61.5% yield) of a mixture of 4,6- and 2,6-diisopropyl-1,3-diaminobenzenes having a melting point of 53-56° C.

PART C

A suitable reaction vessel was charged with a mixture of 630g of the product of Part B and 31.2g of anhydrous cuprous iodide, which was then heated to 145° C. Dimethyldisulfide was added dropwise to maintain a reflux temperature of 145° C., and progress of the reaction was followed by periodically taking aliquots of the reaction mixture and analyzing them by gas chromatography. After 3.5 hours, 620 mL of dimethyldisulfide had been added and no further reaction was apparent.

The mixture was then cooled to 110° C., 33g of solid NaOH was added, and stirring and heating were continued for one hour, after which the mixture was filtered. The filtrate was stripped of excess dimethyldisulfide on a rotary evaporator and the residue flashed in vacuum from 1% solid NaOH. The reaction resulted in a 95.8% yield of a red-colored liquid which GC and GC/MS analyses showed to contain 99.6% of a 5.5/1 mixture of 2-methylthio-4,6-diisopropyl-1,3-diaminobenzene and 4-methyl-thio-2,6-diisopropyl-1,3-diaminobenzene.

EXAMPLE II

PART A

Parts A and B of Example I were essentially repeated except that the starting reaction mixture was obtained by adding a mixture of b 1720g of 70% nitric acid and 12,285g of concentrated sulfuric acid to 1379g of m-xylene, and the temperature maintained for the nitration reaction was 10° C. The nitrution and hydrogenation resulted in the formation of 1275g (72.1% yield) of a mixture of 4,6- and 2,6-dimenthyl 1,3-diaminobenzenes.

PART B

The procedures of EXAMPLE I, Part C, were used to prepare and recover a product from the reaction of 400 mL of dimethyldisulfide with 330g of the product of PART A in the presence of 17.3g of the product of Part A in the prsence of 17.3g of cuprous iodide. The reaction resulted in a 91.6% yield of a waxy, yellow solid which melted at 73-77° C. and contained 97.1% of a 1.4/1 mixture of 2-methylthio-4,6-dimethyl-1,3-diaminobenzene and 4-methylthio-2,6-dimethyl-1,3-diaminobenzene.

It is obvious that many variation may be made in the products and processes set forth above withouth departing from the spirit and scope of this invention.

What is claimed is:

1. A polymer prepared by reacting (1) an organic polyisocyanate and an active hydrogen-containing organic compound or (2) a prepolymer thereof having a free -NCO content of at least 0.1% by weight with (3) a chain extender corresponding to the formula:

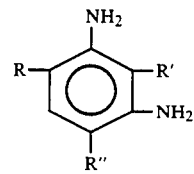

wherein two of the R, R', and R" substituents are alkyl groups containing 1-6 carbons and the other substituent is a hydrocarbylthio group containing 1-6 carbons.

2. The polymer of claim 1 which is a polyurethane.
3. The polymer of claim 1 which is a polyurea.
4. The polymer of claim 1 which is a urethane-urea polymer.
5. The polymer of claim 1 wherein the material reacted with the chain extender is a diphenylmethanediisocyanate prepolymer.
6. The polymer of claim 1 wherein the material reacted with the chain extender is a toluenediisocyanate prepolymer.
7. The polymer of claim 1 wherein two the the R, R', and R" substituents in the chain extender are alkyl groups containing 1-3 carbons and the other substituents is an alkylthio group containing 1-3 carbons.
8. The polymer of claim 7 wherein the chain extender is a 2-alkylthio-4,6-dialkyl-1,3-diaminobenzene and/or 4-alkylthio-2,6-dialkyl-2,3-diaminobenzene.

* * * * *